United States Patent [19]
Köber

[11] 4,281,548
[45] Aug. 4, 1981

[54] METHOD OF TESTING ROTATIONALLY SYMMETRICAL BODIES, ESPECIALLY BALLS, FOR DEFECTS

[75] Inventor: Hans Köber, Schwebheim, Fed. Rep. of Germany

[73] Assignee: Kugelfischer Georg Schäfer & Co., Schweinfurt, Fed. Rep. of Germany

[21] Appl. No.: 84,755

[22] Filed: Oct. 15, 1979

[51] Int. Cl.³ ............................................. G01N 29/04
[52] U.S. Cl. .......................................... 73/593; 73/660
[58] Field of Search .................................. 73/593, 660

[56] References Cited
FOREIGN PATENT DOCUMENTS
2535019 10/1977 Fed. Rep. of Germany ............. 73/593

*Primary Examiner*—Anthony V. Ciarlante
*Attorney, Agent, or Firm*—Karl F. Ross

[57] ABSTRACT

A method of testing rotary bodies, such as balls, for ball bearings, in which the body on a layer of a coupling liquid is subjected to ultrasonic waves transmitted through the ultrasonic liquid and the reflections are measured and displayed. According to the invention the bodies are freely movable in a seat while being immersed in the liquid and jets of the liquid open tangentially into the region between the body and the seat and are intermittently pulsed so that the body undergoes multiaxial rotation.

7 Claims, 3 Drawing Figures

METHOD OF TESTING ROTATIONALLY SYMMETRICAL BODIES, ESPECIALLY BALLS, FOR DEFECTS

FIELD OF THE INVENTION

The present invention relates to a method of testing rotationally symmetric bodies, especially balls, for defects of material and manufacture, e.g. surface and subsurface flaws, eccentricities and the like.

BACKGROUND OF THE INVENTION

In the German patent document (Auslegeschrift) No. 25 35 019 there is described a process for the testing of rotationally symmetrical bodies which can be used in rolling bearings for material and manufacturing defects or flaws.

In this system, the body to be subjected to testing is mounted on the concavity forming a seat or recess on a cushion or layer of a liquid forming a sound-wave coupling medium, the seat constituting part of a body focusing ultrasonic acoustic energy upon the rolling body from an ultrasonic transducer. The body is surrounded by the liquid and motion is imparted to the body by a tangential jet of the liquid opening into the clearance between the seat and the body. Reflected ultrasonic waves are collected and displayed, upon separation from the applied ultrasonic signal, and the reflected signals can be displayed, e.g. on an oscilloscope or by oscillography to reveal surface and subsurface flaws resulting from material or manufacturing defects, roughness, eccentricity, etc.

It has been found that this system, while otherwise highly effective, does not provide complete satisfaction because not every point on the surface of a ball, for example, will be juxtaposed properly with the measuring unit.

OBJECTS OF THE INVENTION

It is, therefore, the principal object of the present invention to provide an improved method of operating a device for the testing of rotationally symmetrical bodies as described in the aforementioned document whereby the above-mentioned disadvantage is obviated.

Another object of the invention is to provide an improved method of testing rotationally symmetrical bodies, especially bearing balls, for material and manufacturing flaws which can apply to all regions of the surface of such bodies.

Yet another object of the invention is to provide an improved method of displacing such rotationally symmetrical bodies for the purposes described.

SUMMARY OF THE INVENTION

These objects and others which will become more readily apparent hereinafter, are attained in a testing method of the type otherwise completely described in the aforementioned document, i.e. a method in which the rotationally symmetrical body is received in an acoustic coupling liquid in a seat or recess and is subjected to focused ultrasonic signals while the body is displaced at least in part by introducing a tangential jet of this liquid into the clearance between the body and the seat reflected ultrasonic waves from the body being analyzed to reveal any defects. According to the invention, a jet introduced tangentially into this clearance is intermittent, i.e. is interrupted or pulsed.

Advantageously, a plurality of such jets open into the clearance and each of the jets is interrupted or pulsed, i.e. is intermittent in the manner described, with the interruption cadance out of phase for the interrupted jets. Alternatively, the jet velocity can be varied periodically with time at one or more of these jets.

It has been found that the intermittent application of the liquid jets to the ball imparts a multiaxial rotation to the latter so that in a relatively brief time, every point of the ball surface is juxtaposed with the axis of the measuring wave source. In addition to normal rotation as established in the manner described in the aforementioned document, therefore, the ball is subjected to a precession which is superimposed on the rotation so that after a short period of time the ball is scanned by the ultrasonic waves from all angles. One jet opens or all of the jets open tangentially into the clearance out of an equatorial plane of the ball through the instantaneous axes of rotation thereof.

With interruption or variation in the jet velocity, the body is intermittently shifted and re-entrained in the liquid cushion with intermittent stopping or slowing and acceleration in a practically uniform manner especially when the pulses are effected at a higher rate, e.g. from 1 to 50 times per second.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
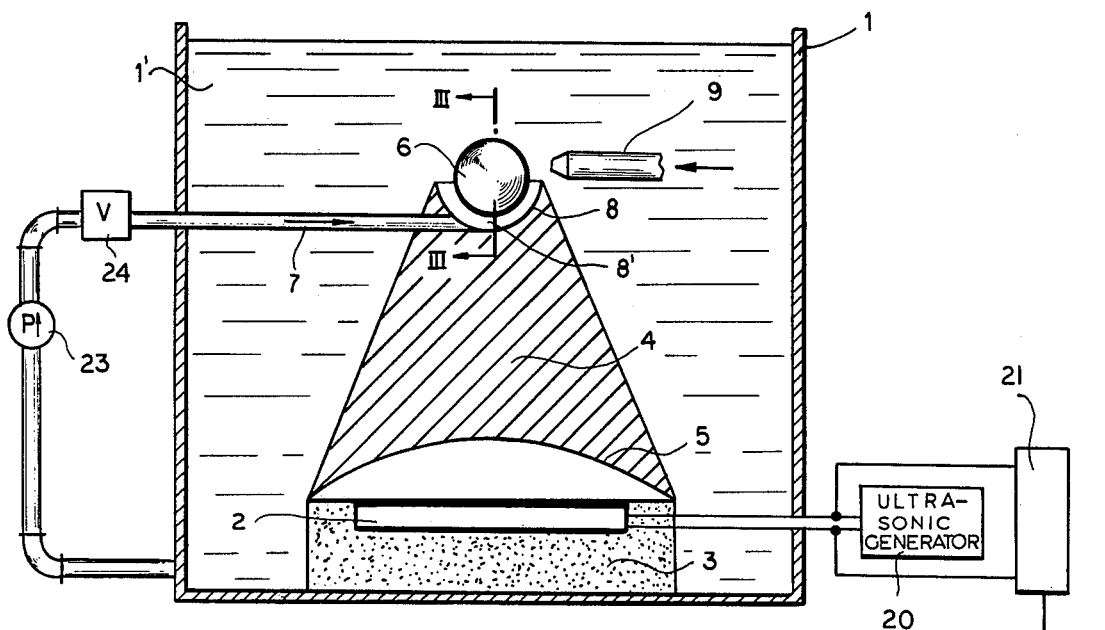
FIG. 1 is a diagrammatic vertical section through an apparatus for carrying out the present invention, partly seen in block diagram form.
Figure 3:
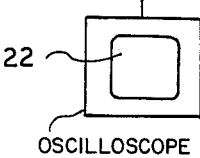
FIG. 3 is a section taken along the line III—III of FIG. 1.

At the outset it should be noted that the testing method as far as the overall structure of the device and the method of operating same is the same as that which has been described in German Pat. No. 25 35 019 except as otherwise indicated below. In other words, the mode of operation, except for the improved precession drive technique, is identical to that set forth in the above-identified document included herein by reference.

As in the German patent document, the apparatus includes a vessel 1 filled with a coupling liquid 1' so that the rolling body or ball 6 is surrounded on all sides by the coupling liquid.

An ultrasonic transducer 2 is disposed in a bed of vibration-damping material 3 and serves as a transmitter for the ultrasonic energy of a given frequency and as receiver.

Above the transducer 2 there is provided a coupling body 4 of upwardly converging frustoconical configuration and having a lens-shaped downward concavity 5 on its underside to focus the ultrasonic energy axially upwardly onto the underside of the roller body 6.

At the small diameter upper end, the body 4 is provided with a concavity or seat 8 of hemispherical configuration and, as can be seen in FIG. 1, a single nozzle 7 can open tangentially to the surface of this seat into the clearance 8' between the ball and the body 4.

Within this clearance, therefore, a hydrodynamic-hydrostatic liquid layer is formed which couples the acoustic energy to the ball, sets the latter in rotation and (in the improvement of the invention) induces a precession as will be discussed in further detail below. A nozzle 7 is provided, once a test is completed, to blow the ball 6 out of the socket so that the apparatus will be available for the next ball to be tested.

The acoustic energy of a given frequency is applied to the ball 1 and sweeps the entire surface of the latter when it receives multiaxial rotation and is precessed in accordance with this invention from a constant frequency generated 20. The reflected sound waves are analyzed by a filter 21 which removes the applied frequency and applies an output signal representing the surface characteristics to an oscilloscope 22.

Figure 2:
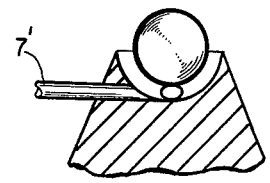
FIG. 2 is a plan view thereof.

As can be seen from FIG. 1, the nozzle 7 can be fed by a pump 23 through a valve 24 which can be pulsed to produce the intermittent jet or a variation in the jet velocity as described. When the jet velocity falls, the center of the ball drops and when the full jet velocity is restored, the center of the ball rises to impose a precession movement on the ball in addition to its rotation in the counterclockwise sense. The precessional movement can be augmented by providing a second jet 7' at right angles to the first, also with an intermittently operated valve 24' or even a third jet 7" with its intermittently operated valve 24" as shown in FIG. 2. The nozzle 7", which also can be used alone (i.e. when nozzles 7 and 7' are not provided or are cut off), opens tangentially into the clearance but does not lie along an equator of the socket or the ball. As a result, the ball is rotated about a multiplicity of axes. When the ball is perfect, a characteristic curve will result on the oscilloscope or on an oscillograph. A flattened portion of the surface and/or subsurface flaw (provided it is not located in the center of the ball) will cause a deviation from this curve in a repetitive manner which is not constant. A defective ball may be ejected by a fluid pulse from nozzle 9 (see German Pat. No. 25 35 019).

Naturally the ball drive system can also be used for the optical or other testing of the surface of a ball.

I claim:

1. In a method of testing a spheroidal workpiece body for surface and subsurface irregularities wherein a jet of a liquid is introduced tangentially into a clearance between said body and a surface spacedly juxtaposed therewith to rotate said body past a location at which the surface is subjected to scanning, the improvement which comprises intermittently varying the velocity of said jet to impart multiaxial rotation to said body during the monitoring.

2. The improvement defined in claim 1 wherein the surface of said body is subjected to scanning during the multiaxial rotation by focusing ultrasonic energy against said body through a frustoconical acoustic transmitter formed with a socket at its upper end, said socket being defined by said surface, said body and said socket being immersed in said liquid, reflected ultrasonic energy from said body serving to indicate surface and/or subsurface irregularities.

3. The improvement defined in claim 2 wherein a plurality of jets of the liquid are directed tangentially into said clearance.

4. The improvement defined in claim 2 wherein said jet opens into said clearance out of an equatorial plane of said body.

5. The improvement defined in claim 2 wherein the velocity of said jet is intermittently varied by interrupting the flow of the jet.

6. The method of driving a spherical workpiece past a location at which the spherical workpiece is scanned for surface and/or subsurface defects, said method comprising hydrostatically and hydrodynamically supporting said workpiece on a layer of liquid in a clearance between a spherically concave socket and the workpiece, introducing a jet of liquid into said clearance tangentially to rotate said workpiece, and intermittently vary the velocity of said jet to induce precessional movement of the workpiece during the rotation thereof.

7. The method defined in claim 6 wherein a plurality of such jets are introduced tangentially into said clearance.

* * * * *